United States Patent
Wang

(10) Patent No.: US 8,915,847 B1
(45) Date of Patent: Dec. 23, 2014

(54) SURGICAL RETRACTOR HOLDER WITH DOWEL PINS

(71) Applicant: Shyh-Jen Wang, Taipei (TW)

(72) Inventor: Shyh-Jen Wang, Taipei (TW)

(73) Assignee: Shyh-Jen Wang, Taipei (TW)

(*) Notice: Subject to any disclaimer, the term of this patent is extended or adjusted under 35 U.S.C. 154(b) by 0 days.

(21) Appl. No.: 13/758,953

(22) Filed: Feb. 4, 2013

(51) Int. Cl.
*A61B 1/32* (2006.01)
*A61B 17/02* (2006.01)

(52) U.S. Cl.
CPC ................. *A61B 17/0293* (2013.01)
USPC .......................... 600/233; 600/231

(58) Field of Classification Search
USPC .............. 600/227–230, 231–233; 24/535, 24/537–538, 575, 577
See application file for complete search history.

(56) References Cited

U.S. PATENT DOCUMENTS

| | | | |
|---|---|---|---|
| 4,254,763 A | 3/1981 | McCready et al. | |
| 4,421,108 A | 12/1983 | Cabrera et al. | |
| 4,424,724 A | 1/1984 | Bookwalter et al. | |
| 4,467,791 A | 8/1984 | Cabrera et al. | |
| 5,375,481 A * | 12/1994 | Cabrera et al. | 74/577 M |
| 5,520,608 A | 5/1996 | Cabrera et al. | |
| 6,241,659 B1 | 6/2001 | Bookwalter et al. | |
| 6,530,883 B2 | 3/2003 | Bookwalter et al. | |
| 6,620,097 B1 | 9/2003 | Bookwalter et al. | |
| 2002/0193666 A1 * | 12/2002 | Sherts et al. | 600/231 |
| 2008/0065082 A1 * | 3/2008 | Chang et al. | 606/85 |

* cited by examiner

*Primary Examiner* — Eduardo C Robert
*Assistant Examiner* — Julianna N Harvey

(57) ABSTRACT

A retractor holder comprises a body poration, a retractor locking portion and a support ring mating portion. The retractor handle can be inserted through a compatible opening bore extending through body portion. The locking portion has a spring-loaded pawl where the leading edge of pawl can mate with teeth of the retractor handle to lock the retractor handle in a fixed position. The mating portion has a slot with an opening on the opposite surface from the leading edge of the pawl to slide onto the support ring. To improve the problem that prior art retractor holders can not rotate an angle on the support ring, a plurality of dowel pins are set in the slot of the support ring mating portion. Thus, the retractor holder can rotate an angle and keep at least one dowel pin to engage with an indentation on support ring.

8 Claims, 3 Drawing Sheets

SURGICAL RETRACTOR HOLDER WITH DOWEL PINS

FIELD OF THE INVENTION

The present invention relates to a surgical retractor holder, and more particularly, to a plurality of dowel pins to keep the holder from sliding on its support ring when the retractor is rotated.

BACKGROUND OF THE INVENTION

In surgical operations of the abdomen, it is customary to employ a retraction apparatus to retain tissue away from the operative site. The retraction apparatus may include a frame or support ring rests over the patient surrounding the surgical opening and a number of retractors may be movably attached to the frame and flexibly positioned, with various clamping or positioning mechanisms, to reach into the surgical opening and retract surrounding tissue or organs.

By way of example, one system is disclosed in the various US patents, such as U.S. Pat. Nos. 4,254,763; 4,421,108; 4,424,724; 4,467,791; 5,520,608; 5,375,481; 6,241,659 and 6,530,883. In the so-called Bookwalter system, the frame element is a flat support ring with indentations. The support ring is held by a post that clamps to the side rail of the operating table and suspended in a plane above the surgical site. The retractor holder can engage with indentation on the support ring and allow retractor to slide into position.

Such a retractor holder is shown in U.S. Pat. Nos. 4,254,763; 4,421,108 and 4,467,791. The holder includes a spring-loaded pawl to lock the retractor handle in a fixed position and a slot to be slid on to the ring. The slot may incorporate a dowel or other pin with a smooth radius to matingly fit into an indentation on the support ring.

Another retractor holder shown in U.S. Pat. Nos. 4,424,724; 5,375,481; 6,241,459 and 6,530,883 includes a multi-position ratchet mechanism which permits a retractor blade to be rotated into the wound. The retractor holder with ratchet mechanism also has a slot with a dowel pin to engage one of the indentations on the outer circumferential edge of support ring. The engagement of indentation and the dowel pin provides a means for holding the position of retractor holder along the ring.

However, the engagement between the retractor holder, either with or without the multi-position ratchet mechanism, and the support ring is with only one dowel pin to engage with an indentation. Thus, the retractor holder may lose the engagement with the support ring when the holder rotates an angle. The rotation may cause the dowel pin to leave the indentation on the outer circumferential edge of support ring. When losing the engagement, the retractor holder may slide along the circumferential edge of ring. Indeed, the retractor holder with a dowel pin has a difficulty to rotate on the support ring.

To improve the rotation ability on the support ring, U.S. Pat. No. 6,241,659 further discloses the retractor stem has a round cross-section to rotate freely about it axis by an amount less than 45 degrees. However, rotating the retractor stem does not have the same effect as that of the retractor holder. Therefore, U.S. Pat. No. 6,620,097 tries to build a three-dimensional ratchet mechanism for retractor holder. However, the 3D retractor holder further needs a rotator indexing body and its mating member. It, somehow, complicates the structure, manufacture and assembly. Moreover, the 3D retractor holder utilizes a ball plunger to seat against the one of the indentations on the support ring. Since there is no locking device to secure the holder on the ring, the holder still has a difficulty to rotate on the support ring.

Because of the necessity of rotating the retractor holder on the support ring to hold tissue or organ in position, it is cumbersome to design a stopping device or lock device to secure the holder on the ring. It would be advantageous to have a mechanism in which the retractor holder can rotate and still hold on the support ring without slip. Thus, a retractor with such as a holder can rotate an angle on the support ring and hold the tissue in the wound.

SUMMARY OF THE INVENTION

The present invention provides a mechanism for a retractor holder such that the holder can rotate an angle on the support ring and hold the tissue in the wound.

DETAILED DESCRIPTION OF THE PREFERRED EMBODIMENT

Figure 1:
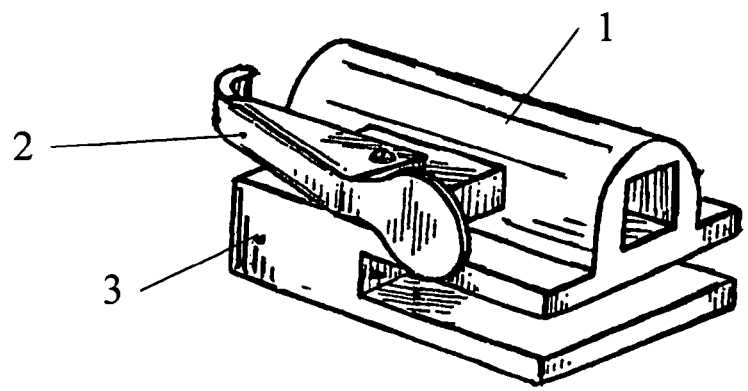
FIG. 1 shows a perspective view of the prior art retractor holder.

Referring to FIG. 1, there is shown a prior art retractor holder similar to that shown in U.S. Pat. No. 4,467,791. The retractor holder mainly includes a body poration 1, a retractor locking portion 2 and a support ring mating portion 3. The body portion 1 has a compatible opening bore, where a retractor handle can insert through. The retractor locking portion 2 has a pawl mating with teeth on the retractor handle, and thus can lock the retractor in a fixed position. The support ring mating portion 3 has a slot incorporating a dowel pin (not shown in FIG. 1) to engage one of the indentations on the outer circumferential edge of support ring.

Figure 2:
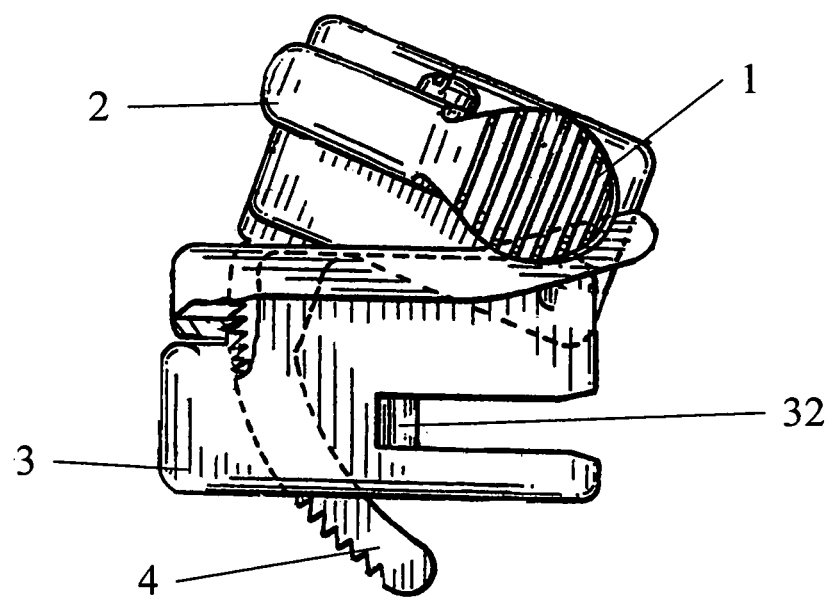
FIG. 2 shows a side elevation of the prior art retractor holder with multi-position ratchet mechanism.

The prior art retractor holder, shown in FIG. 2, further includes a multi-position ratchet mechanism 4, which is the same as that shown in U.S. Pat. No. 5,375,481. The multi-position ratchet mechanism 4 mainly includes a curved ratchet, which may slide in and out of opening on support ring mating portion 3, and a ratchet release bar which can engage with the ratchet to fix body poration 1 in position. From the side elevation shown in FIG. 2, one can clearly see a dowel pin 32 in the slot of the support ring mating portion 3.

Figure 5:
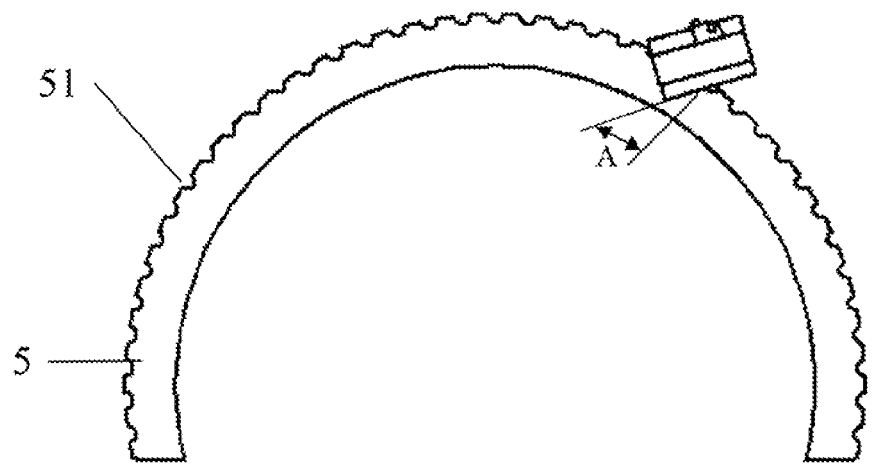
FIG. 5 shows a top plan view of the present invention rotating an angle on the support ring.

Now referring to FIG. 5, the prior art retractor holders, shown in either FIG. 1 and FIG. 2, can not rotate an angle on the support ring 5. Especially when the rotation causing the only one dowel pin not to engage with the support ring, the retractor holder will slip on the outer circumferential edge of the ring. However, this problem has not been either identified or solved adequately. For example, '791 and '481 patents were issued on Aug. 28, 1984 and Dec. 27, 1994, respectively. So far, to the best of this applicant's knowledge, it has been a long time and none effort has been added to the retractor holder so that the holder can rotate an angle on the support ring and still keep holding the tissue in the wound. The so-called 3D retractor holder, as demonstrated on U.S. Pat. No. 6,620,097, introduces more parts and it still can not rotate an angle on the support ring.

Therefore, to keep the retractor holder to rotate an angle on the support ring and still to hold the tissue in the wound, we need a mechanism which at least one dowel pin of the holder can always engages with one of the indentations on the outer circumferential edge of support ring. To meet this requirement, this invention designs the retractor holder which has at least two dowel pins in the slot and the pins are separated by a pitch. Pitch is defined as the distance between a point on one indentation and the corresponding point on an adjacent indentation of the support ring, as the p shown in FIG. 6.

Figure 3:
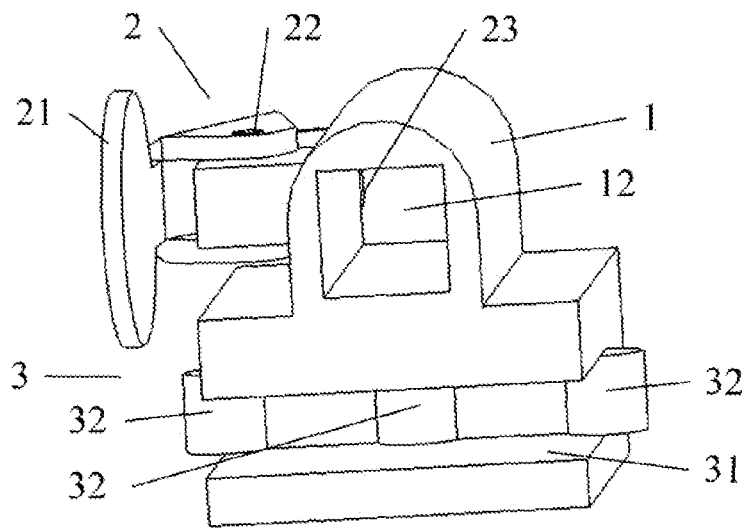
FIG. 3 shows a perspective view of the present invention without multi-position ratchet mechanism.
Figure 6:
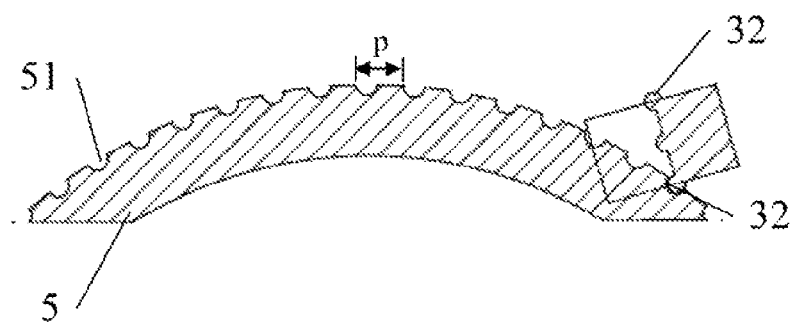
FIG. 6 shows a cross section view of this invention shown in FIG. 5.

One embodiment of this current invention is shown in FIG. 3 which is similar to that shown in '791 patent. This retractor holder currently designed includes a body poration 1, a retractor locking portion 2 and a support ring mating portion 3. A retractor (not shown in FIG. 3) can be used for restraining tissue or organs during the surgical procedure. The handle of the retractor has multiple spaced ratchet teeth which are spaced to provide small incremental adjustments of the handle. Handle is inserted through a compatible opening bore 12 extending through body portion 1, as seen in FIG. 3. Teeth on the handle face a spring-loaded pawl 21 which is connected by a pivot pin 22 to retractor locking portion 2. The leading edge 23 of pawl 21 mates with teeth of the handle and thereby locks the handle in a fixed position. The retractor holder is slid onto support ring 5 by means of a slot 31 through the mating portion 3. Slot 31 is open to the opposite surface from that surface which leading edge 23 of the pawl extends. As seen in FIG. 3, slot 31 may incorporate three dowel pins 32. Each pin is with a smooth radius and separated by a pitch. Thus, at least one of the dowel pins can matingly fit into an indentation 51 on support ring 5 to hold the retractor holder securely onto the support ring 5. Because of a plurality of dowel pins 32, the retractor holder can rotate an angle and still keep at least one pin 32 to engage with an indentation 51 on support ring 5, as shown in FIG. 5 and FIG. 6. The rotation angle, as marked A in FIG. 5, can be turned either right or left up to 70 to 80 degrees. The largest angle preferred is around 50~60 degrees. However, the prior arts with only one dowel pin can rotate only up to 10 to 15 degrees. Actually, the prior arts will indeed slide on the support ring when it is rotated an angle.

Figure 4:
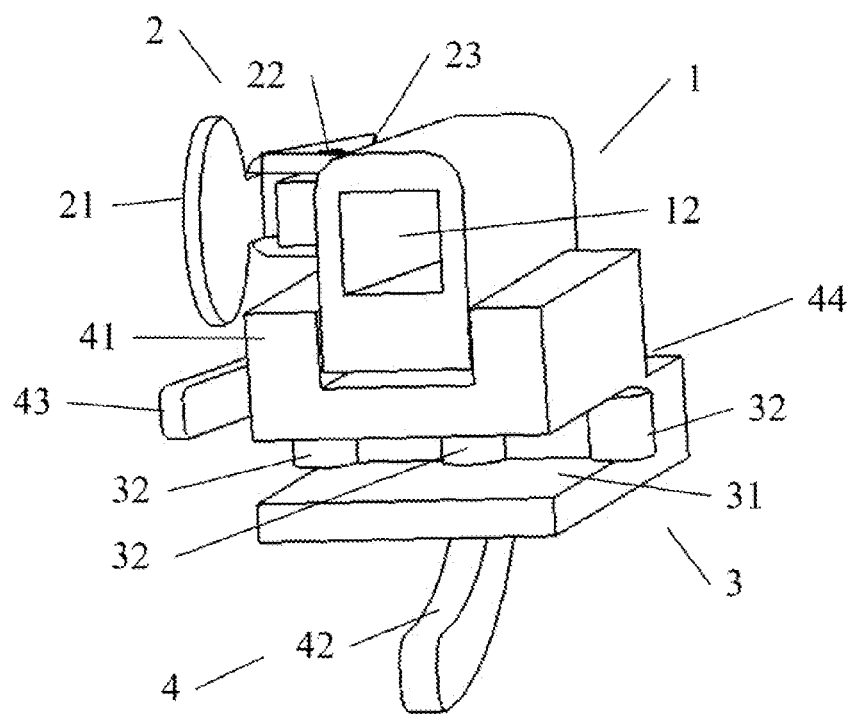
FIG. 4 shows a perspective view of the present invention with multi-position ratchet mechanism.

Another embodiment of this current invention, shown in FIG. 4, also includes a body poration 1, a retractor locking portion 2 and a support ring mating portion 3, as described above and in FIG. 3. Furthermore, the holder encomposes a multi-position ratchet mechanism 4 which is similar to that shown in '481 patent. The ratchet mechanism 4 includes a pivot housing 41 extended from the mating portion 3 to pivot with the body portion 1, a curved ratchet 42 from the bottom of the body portion 1 toward support ring mating portion 3 and a ratchet release bar 43 which is affixed to the mating portion 3. The rear surface 44 of the mating portion 3 includes a vertical slot 45 (not shown in FIG. 4) which receives curved ratchet 42. The interior transverse wall of slot 45 is curved to the same extent as curved ratchet 42 so that curved ratchet 42 may slide easily in and out of slot 45 as body poration 1 pivots about pivot housing 41. The ratchet release bar 43 is generally L-shaped and affixed by a pin (not shown in FIG. 4) which extends through bore and is retained in a bore on the mating portion 3. There is a cut out portion on one side of the ratchet release bar to engage with the curved ratchet 42. When the cut out portion engages the teeth in the curved ratchet 42, the ratchet pivot housing is fixed in position. It can be seen that multi-position ratchet mechanism 4 permits a retractor blade to be pivoted in or away from the would, by exerting pressure on the ratchet release bar 43.

Moreover, the embodiment shown in FIG. 4 also incorporate three dowel pins 32. Each pin is with a smooth radius and separated by a pitch. Thus, at least one of the dowel pins can matingly fit into an indentation 51 to hold the retractor holder securely onto the support ring 5. Because of a plurality of dowel pins 32, the retractor holder can rotate an angle on the support ring 5 and still keep at least one dowel pin 32 to engage with an indentation 51 on support ring 5, as shown in FIG. 5 and FIG. 6.

The embodiments shown in FIG. 3 and FIG. 4 incorporate three dowel pions. Moreover, a retractor holder with two dowel pins may also work well. The pins of the two-pin retractor holder should be separated at least one pitch or two pitches preferred. It should be mentioned that, other than a full circle, the shape of support ring may be somewhat like an ellipse which includes two half circle portions and two straight line portions. The pitches between indentations 51 in circle portions is slightly larger than that in straight line portions. Thus, to fit in both portions, the retractor holder with two or three dowel pins 32 may be designed to have smaller radius than that of indentation 51 on support ring 5. In other words, the radius of the dowel pin 32 should be small enough to tolerate the pitch difference between indentations 51 on support ring 5. Thus, the dowel pins 32 can engage with the indentations 51 on support ring 5. On the other hand, to incorporate dowel pins 32 to the retractor holder, one can drill holes to fit in with, weld or use other manufacture methods, such as casting.

Furthermore, the applicant would like stress the nonobviousness of this application. As mentioned above, prior art retractor holders, either with a multi-position ratchet mechanism or not, have been disclosed and used for more than ten years. None effort has been added to the retractor holder for these long period of time so that the holder can rotate an angle on the support ring and still keep holding the tissue in the wound. A person skill in the art would not modify these prior arts by adding more dowel pins. Moreover, this current invention with a plurality of dowel pins may have two or three pins to simultaneously engage with the indentations on support ring and thus improve the stability of the engagement between the retractor holder and the support ring.

Comparing with prior arts, this invention incorporates at least two dowel pins but the prior arts have only one pin. The retractor holder with a plurality of dowel pins can rotate an angle on the support ring and still keep holding the tissue in the wound but the prior arts do not have such a function. Other the rotating function, a plurality of pins retractor holder can also result in the improvement of the engagement stability of the holder to the support ring. Therefore, the function-way-result analysis would also demonstrate the nonobviousness of this application over prior arts.

Moreover, this invention is not just simply to add two or three dowel pins. Each pin should be separated by one pitch or two pitches to avoid interference form the indentations on support ring.

The present invention has been described in conjunction with the preferred embodiment. Those skilled in the art will appreciate that other modifications and changes may be made in the present embodiment without departing from the present invention.

What is claimed is:

1. A retractor holder to engage with a support ring, said retractor holder comprising:
   a body portion;

a retractor locking portion;
a multi-position ratchet mechanism; and
a support ring mating portion;
said body portion having a bore for insertion of a retractor handle;
said retractor locking portion having a spring-loaded pawl, a leading edge of said pawl configured to mate with teeth of the retractor handle to lock the retractor handle in a fixed position;
said multi-position ratchet mechanism including a pivot housing extending from said support ring mating portion to pivot with said body portion for pivoting in or away from a wound;
said support ring mating portion having a slot with an opening on an opposite surface from said leading edge of said pawl to slide onto said support ring; and
a plurality of dowel pins in said slot of said support ring mating portion, each dowel pin having a radius to engage with an indentation on said support ring and a portion of each of two pins of said plurality of dowel pins extending externally of said slot.

2. The retractor holder of claim 1 wherein said multi-position ratchet mechanism includes a curved ratchet extending from the bottom of said body portion toward said support ring mating portion and a ratchet release bar which is affixed to said mating portion, said the ratchet release bar is L-shaped and affixed by a pin on said mating portion such that a retractor blade may be pivoted in or away from a wound by exerting pressure on said ratchet release bar.

3. The retractor holder of claim 1 wherein said plurality of dowel pins comprises two or three pins.

4. The retractor holder of claim 1 wherein said dowel pins are separated by a pitch or two pitches.

5. The retractor holder of claim 1 wherein a radius of each of said dowel pins is smaller than that of an indentation on said support ring such that a dowel pin can, engage with an indentation on said support ring.

6. The retractor holder of claim 1 wherein said retractor holder can rotate to an angle on said support ring such that at least one dowel pin remains engaged with an indentation on said support ring.

7. The retractor holder of claim 6 wherein the maximum angle that said retractor holder can rotate is 80 degrees.

8. The retractor holder of claim 1 wherein said dowel pins are fitted, welded or casted in said slot of said support ring mating portion.

* * * * *